United States Patent
Anderson et al.

(10) Patent No.: US 11,103,358 B2
(45) Date of Patent: Aug. 31, 2021

(54) JOINT IMPLANTS AND METHODS

(71) Applicant: Biomet Manufacturing, LLC, Warsaw, IN (US)

(72) Inventors: David M. Anderson, Winona Lake, IN (US); Brian K. Berelsman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/349,752

(22) Filed: Nov. 11, 2016

(65) Prior Publication Data
US 2017/0135821 A1 May 18, 2017

Related U.S. Application Data

(60) Provisional application No. 62/254,282, filed on Nov. 12, 2015.

(51) Int. Cl.
*A61F 2/42* (2006.01)
*A61F 2/38* (2006.01)
(Continued)

(52) U.S. Cl.
CPC ........ *A61F 2/4202* (2013.01); *A61B 17/1775* (2016.11); *A61F 2/28* (2013.01);
(Continued)

(58) Field of Classification Search
CPC ........ A61F 2/4081; A61F 2/4014; A61F 2/40; A61F 2002/30332; A61F 2002/30604;
(Continued)

(56) References Cited

U.S. PATENT DOCUMENTS 5,489,310 A * 2/1996 Mikhail ............. A61B 17/1684
623/19.11
6,663,669 B1 * 12/2003 Reiley .................... A61B 17/15
623/21.18
(Continued)

FOREIGN PATENT DOCUMENTS

CN 101448533 6/2009
CN 101522131 9/2009
(Continued)

OTHER PUBLICATIONS

"International Application Serial No. PCT/US2016/061627, International Search Report dated Feb. 10, 2017", 6 pgs.
(Continued)

*Primary Examiner* — Ann Schillinger
(74) *Attorney, Agent, or Firm* — Schwegman Lundberg & Woessner, P.A.

(57) ABSTRACT

Implementations described herein provide for a bone implant having a cylindrical member and an articulating member. The cylindrical member extends along an implant axis from a first end to an opposed second end thereof. The cylindrical member has a void disposed therein extending from the first end towards the second end. The cylindrical member has an interconnected open-pore structure for promoting bone tissue in-growth. The articulating member has an articulating portion and a core portion extending away from the articulating portion. The articulating member is coupled to the cylindrical member such that the core portion extends into the void disposed in the cylindrical member and the articulating portion is positioned adjacent the first surface of the cylindrical member and extends radially outward from the implant axis to cover the first surface of the cylindrical member.

18 Claims, 9 Drawing Sheets

(51) Int. Cl.
  *A61F 2/30* (2006.01)
  *A61F 2/28* (2006.01)
  *A61B 17/17* (2006.01)
  *A61F 2/46* (2006.01)

(52) U.S. Cl.
  CPC ............ *A61F 2/30* (2013.01); *A61F 2/30734* (2013.01); *A61F 2/30749* (2013.01); *A61F 2/30756* (2013.01); *A61F 2/4606* (2013.01); *A61F 2002/30011* (2013.01); *A61F 2002/3085* (2013.01); *A61F 2002/3092* (2013.01); *A61F 2002/30224* (2013.01); *A61F 2002/30327* (2013.01); *A61F 2002/30331* (2013.01); *A61F 2002/30754* (2013.01); *A61F 2002/4205* (2013.01); *A61F 2002/4207* (2013.01)

(58) Field of Classification Search
  CPC .... A61F 2002/4022; A61F 2002/30433; A61F 2/4059; A61F 2/389; A61F 2/4612
  See application file for complete search history.

(56) References Cited

U.S. PATENT DOCUMENTS

| | | | |
|---|---|---|---|
| 6,939,380 | B2 | 9/2005 | Guzman |
| 9,498,345 | B2* | 11/2016 | Burkhead, Jr. ....... A61F 2/4081 |
| 2005/0288792 | A1* | 12/2005 | Landes ................. A61F 2/4644 623/21.18 |
| 2007/0219637 | A1 | 9/2007 | Berelsman et al. |
| 2009/0312842 | A1 | 12/2009 | Bursac et al. |
| 2010/0009103 | A1 | 1/2010 | Kuboki et al. |
| 2010/0268337 | A1 | 10/2010 | Gordon et al. |
| 2011/0035013 | A1* | 2/2011 | Winslow ............... A61F 2/4003 623/19.13 |
| 2011/0035019 | A1* | 2/2011 | Goswami .............. A61F 2/4202 623/21.18 |
| 2011/0070271 | A1 | 3/2011 | Truncale et al. |
| 2012/0172880 | A1 | 7/2012 | Dee |
| 2012/0245701 | A1 | 9/2012 | Zak et al. |
| 2016/0089245 | A1* | 3/2016 | Early .................... A61F 2/4202 623/21.18 |

FOREIGN PATENT DOCUMENTS

| | | |
|---|---|---|
| CN | 108366860 A | 8/2018 |
| JP | 2004520855 A | 7/2004 |
| JP | 2012522571 | 9/2012 |
| WO | WO-0130264 A2 | 5/2001 |
| WO | 2010144065 | 12/2010 |
| WO | WO-2017083718 A1 | 5/2017 |

OTHER PUBLICATIONS

"International Application Serial No. PCT/US2016/061627, Written Opinion dated Feb. 10, 2017", 6 pgs.

"Australian Application Serial No. 2016353265, First Examination Report dated Oct. 23, 2018", 4 pgs.

"Australian Application Serial No. 2016353265, Response filed Jun. 28, 2019 to Subsequent Examiners Report dated Apr. 8, 2019", 20 pgs.

"Australian Application Serial No. 2016353265, Subsequent Examiners Report dated Apr. 8, 2019", 5 pgs.

"Canadian Application Serial No. 3,005,228, Office Action dated Feb. 1, 2019", 4 pgs.

"Canadian Application Serial No. 3,005,228, Response filed Jul. 31, 2019 to Office Action dated Feb. 1, 2019", 10 pgs.

"Chinese Application Serial No. 201680072751.1, Office Action dated Jun. 24, 2019", w English translation, 14 pgs.

"Japanese Application Serial No. 2018-524417, Notification of Reasons for Rejection dated Jul. 2, 2019", W English Translation, 15 pgs.

"Canadian Application Serial No. 3,055,228, Office Action dated Sep. 11, 2019", 4 pgs.

"Chinese Application Serial No. 201680072751.1, Response filed Sep. 18, 2019 to Office Action dated Jun. 24, 2019", (W/ English Claims), 11 pgs.

"Japanese Application Serial No. 2018-524417, Notification of Reasons for Rejection dated Nov. 12, 2019", (W/ English Translation), 11 pgs.

"Japanese Application Serial No. 2018-524417, Response filed Oct. 2, 2019 to Notification of Reasons for Rejection dated Jul. 2, 2019", (W/ English Claims), 29 pgs.

"Japanese Application Serial No. 2018-524417, Response filed Feb. 2, 2020 to Notification of Reasons for Rejection dated Nov. 12, 2019", with English claims, 16 pages.

"Canadian Application Serial No. 3,005,228, Response filed Mar. 11, 2020 to Office Action dated Sep. 11, 2019", 4 pages.

"Japanese Application Serial No. 2018-524417, Response filed Oct. 19, 2020 to Examiners Decision of Final Refusal dated Jul. 28, 2020", with English claims, 26 pages.

"Japanese Application Serial No. 2018-524417, Examiners Decision of Final Refusal dated Jul. 28, 2020", with English translation, 7 pages.

* cited by examiner

JOINT IMPLANTS AND METHODS

PRIORITY APPLICATION

This application claims the benefit of priority to U.S. Provisional Application Ser. No. 62/254,282, filed Nov. 12, 2015, the content of which is incorporated hereby by reference in its entirety.

FIELD

The present disclosure relates to joint implants for promoting bony in-growth and associated systems and methods.

BACKGROUND

This section provides background information related to the present disclosure, which is not necessarily prior art.

Osteochondral lesions are a common injury to the ankle and knee regions (as well as other joints) that can be caused by traumatic injury (e.g., a severe sprain). Osteochondral lesions are injuries to the articular joint surface that affect both the bone and the cartilage surrounding the bone. Such lesions can be present at the ankle joint, where the talus meets the tibia, or at the sub-talar joint, where the talus meets the calcaneous. In less severe cases, osteochondral lesions may be treated by restricting activity and simply allowing the injured cartilage and bone to heal. However, some cases will require surgical remedies. Some surgical remedies include conventional bone and cartilage grafting, debridement (i.e. removing damaged cartilage and bone), or microfracture of the lesion. These techniques may be ineffective in treating larger lesions.

SUMMARY

This section provides a general summary of the disclosure, and is not a comprehensive disclosure of its full scope or all of its features.

The present inventors have recognized, among other things, that a problem to be solved can include a solution for effective surgical treatment of large cystic type-V lesions of the talus. The present disclosure provides such a solution through an implant intended for insertion into and replacement of the damaged region of the talus bone and cartilage that promotes bony in-growth while also providing for an articulable joint surface. Accordingly, the present disclosure provides for a bone implant that can comprise a cylindrical member and an articulating member. The cylindrical member can extend along an implant axis from a first end to an opposed second end thereof. The cylindrical member can have a void disposed therein extending from the first end towards the second end. The cylindrical member can comprise an interconnected open-pore structure for promoting bone tissue in-growth. The articulating member can comprise an articulating portion and a core portion extending away from the articulating portion. The articulating member can be coupled to the cylindrical member such that the core portion extends into the void disposed in the cylindrical member and the articulating portion is positioned adjacent the first surface of the cylindrical member and extends radially outward from the implant axis to cover the first surface of the cylindrical member.

In another example, the present disclosure provides for a system comprising a first bone implant and a second bone implant. The first bone implant can comprise a first cylindrical member and a first articulating member. The first cylindrical member can extend along a first implant axis from a first end to an opposed second end thereof. The first cylindrical member can have a void disposed therein extending from the first end towards the second end. The first cylindrical member can comprise an interconnected open-pore structure for promoting bone tissue in-growth. The first articulating member can comprise an articulating portion and a core portion extending away from the articulating portion. The first articulating member can be coupled to the first cylindrical member such that the core portion extends into the void disposed in the first cylindrical member and the articulating portion is positioned adjacent the first surface of the first cylindrical member and extends radially outward from the implant axis to cover the first surface of the first cylindrical member. The second bone implant can comprise a second cylindrical member and an articulating portion. The second cylindrical member can extend along a first implant axis from a first end to an opposed second end thereof. The second cylindrical member can comprise an interconnected open-pore structure for promoting bone tissue in-growth. The outer diameter of the first cylindrical member of the first bone implant can be less than the outer diameter of the second cylindrical member of the second bone implant.

In another example, a method is provided that comprises preparing bone tunnels from outside of the bone to a point within the bone defect. These bone tunnels may be directed with the use of a guide that can contain a targeting arm on a multi-planar positioning jig. The target arm can be placed inside the joint at a position that is optimized for placement of the implant. The jig can then be positioned to contact a portion of the same bone at a point in which a small incision and bone tunnel can be created in order to access the bone defect. Bone tunnels can be created by placing guide wires and then drilling the bone with cannulated drills, reamers, or bone trephines once the guide wire is in place. If two opposing implants are prescribed, the bone tunnel for the second bone and implant can be drilled through the initial bone tunnel of the first bone. Also, if multiple implants are prescribed in the second bone, the corresponding bone tunnels can be drilled into the second bone by rotating the joint and repositioning the lesion and second implant site to be in-line with the first bone tunnel in the first bone. Additionally, multiple bone tunnels could be drilled in the first bone by repositioning the guide on the first bone and placing multiple guide wires and tunnels. The bone tunnels in the first bone may be the same size or slightly larger than the tunnel in the second bone. This can help make the insertion of the implant into the second bone easier. Insertion devices can assist with inserting the implants either through the bone tunnels or through the joint space. It is anticipated that final placement of the implants would occur through the bone tunnels.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 4:
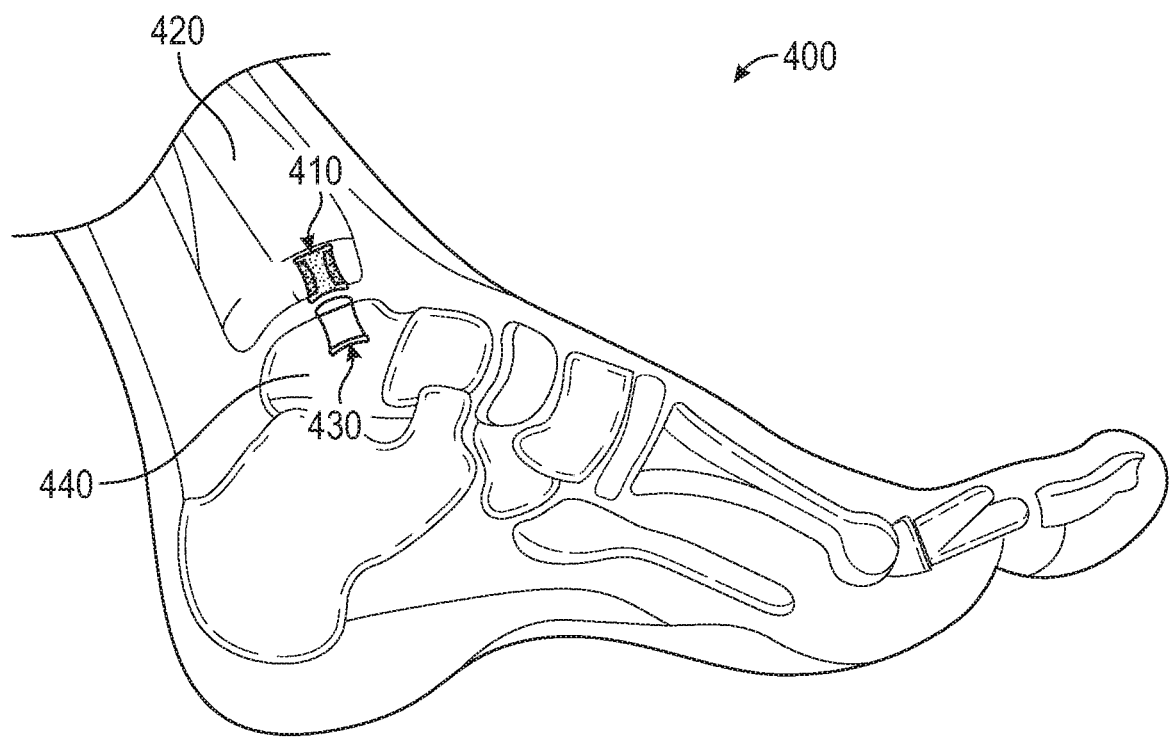

FIG. 4 provides a side view of an implantable joint system according to at least one example of the present description.

Figure 5:
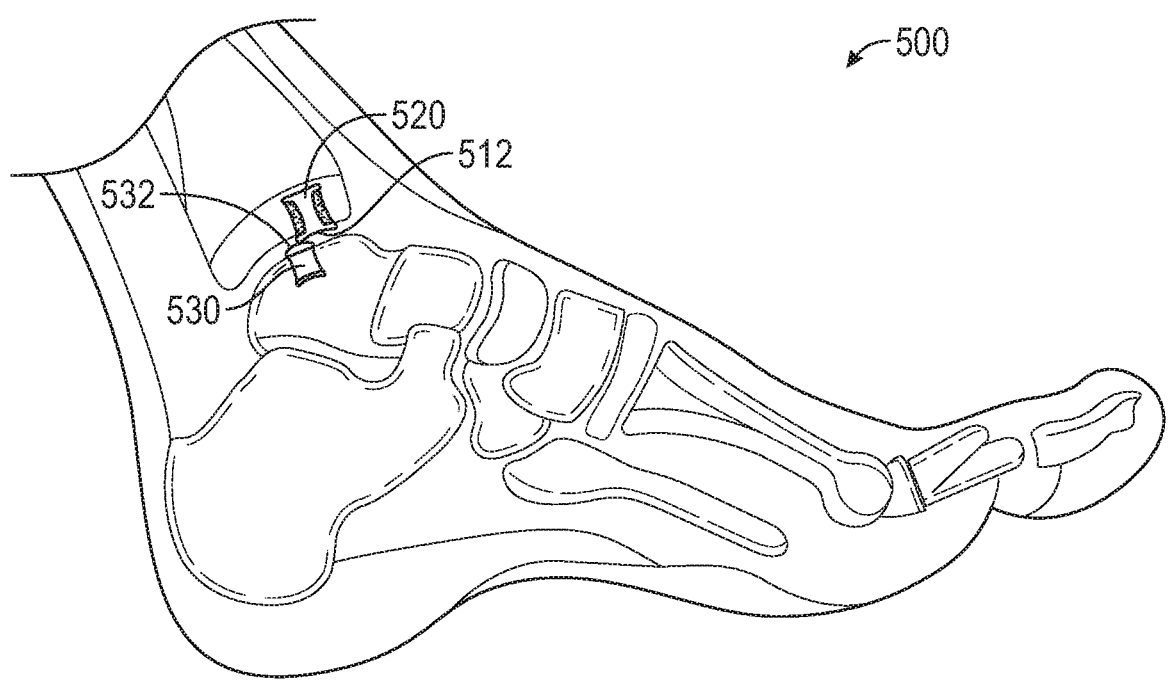

FIG. 5 provides a side view of an implantable joint system according to at least one example of the present description.

Figure 6:
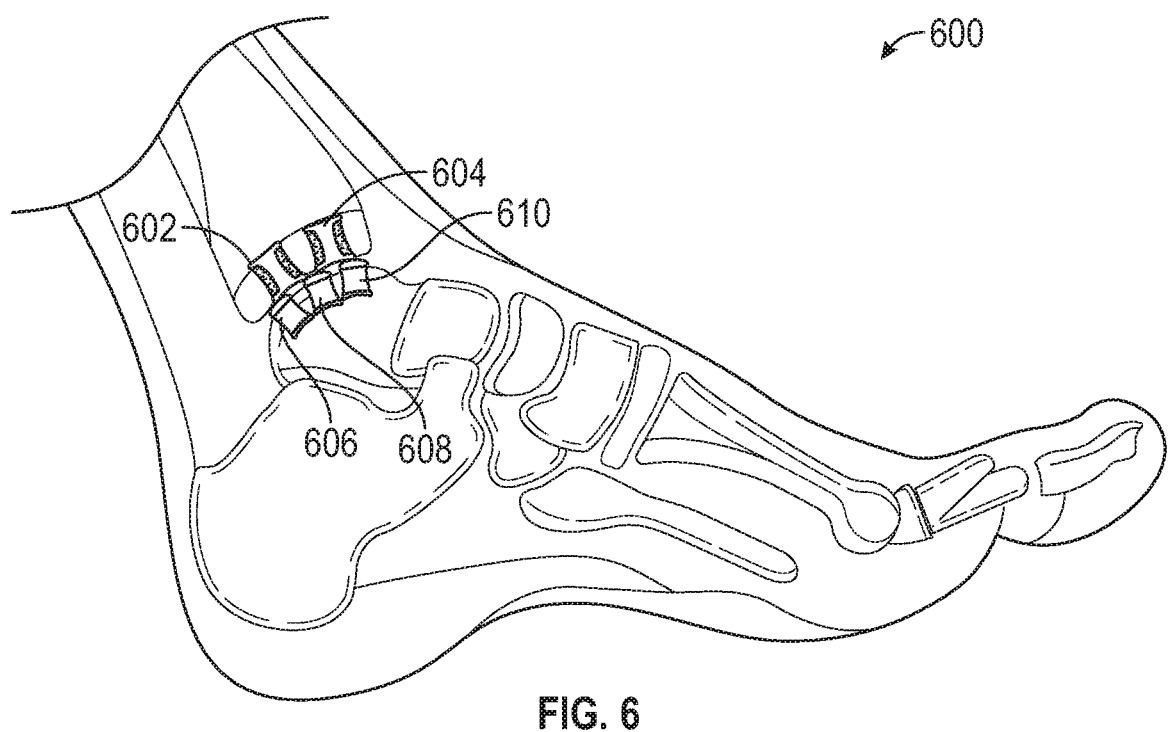

FIG. 6 provides a side view of an implantable joint system according to at least one example of the present description.

Figure 7A:
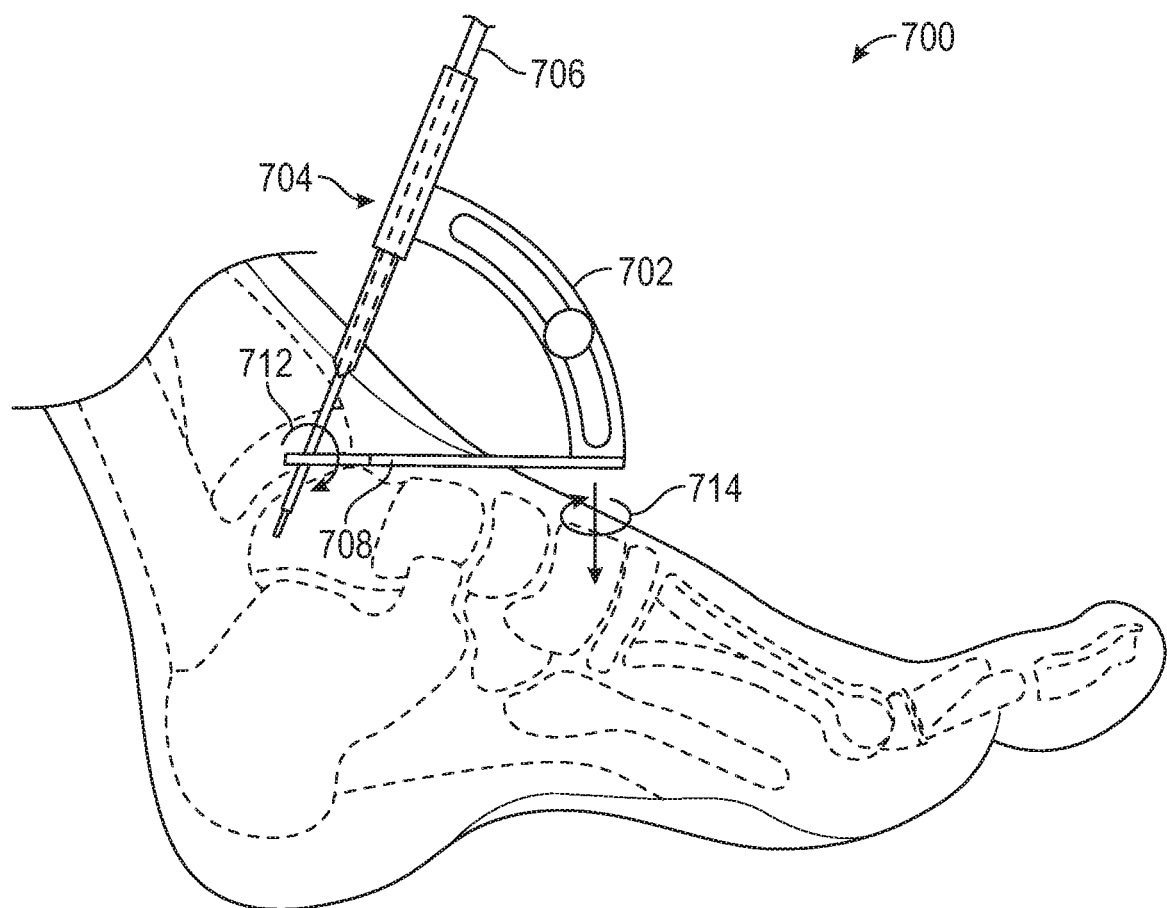

FIG. 7A illustrates one exemplary guide for implanting a bone implant.

Figure 7B:
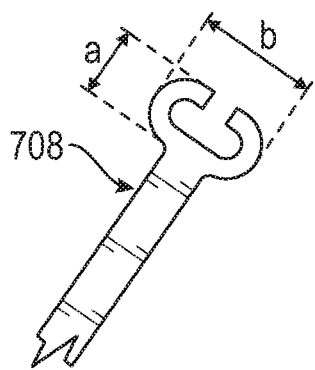

FIG. 7B is a partial perspective view of the guide foot of FIG. 7A.

Figure 8A:
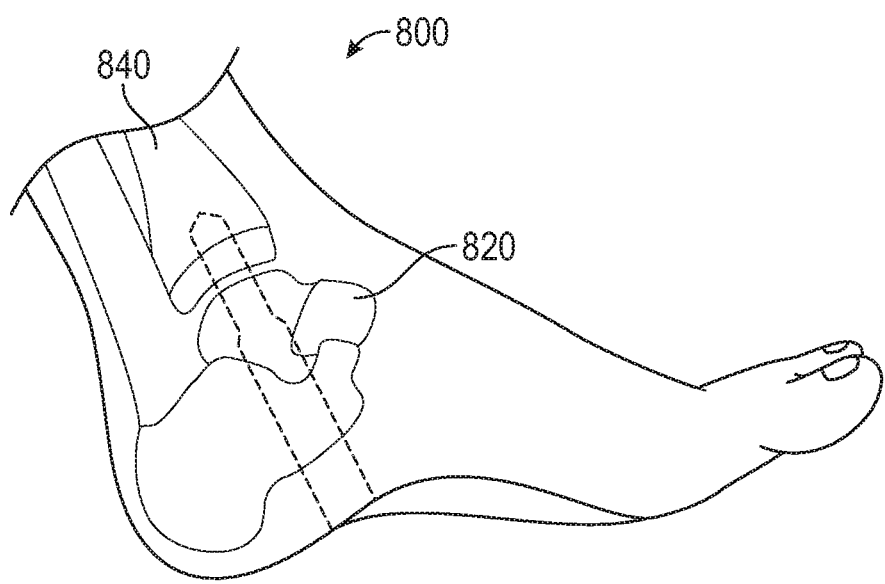
Figure 8B:
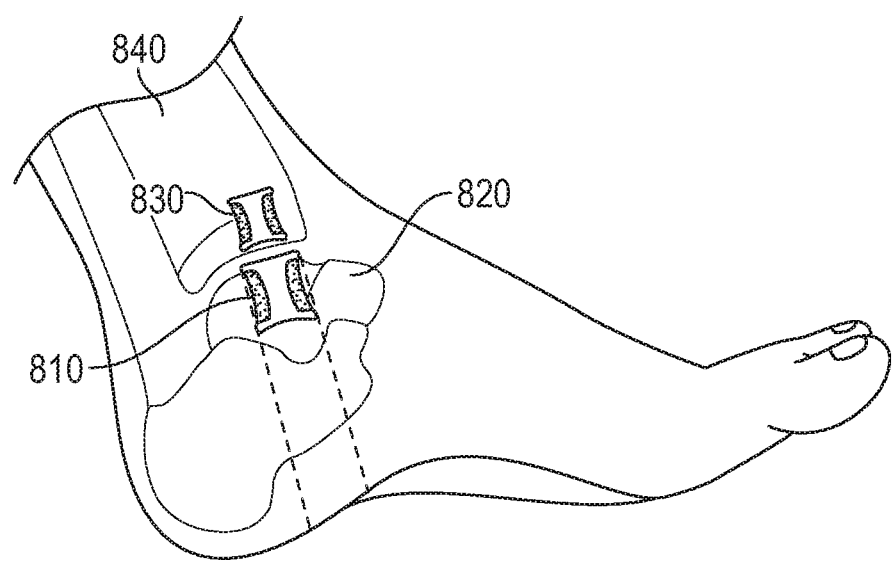

FIGS. 8A and 8B illustrate one exemplary method for implanting bone implants.

Figure 9:
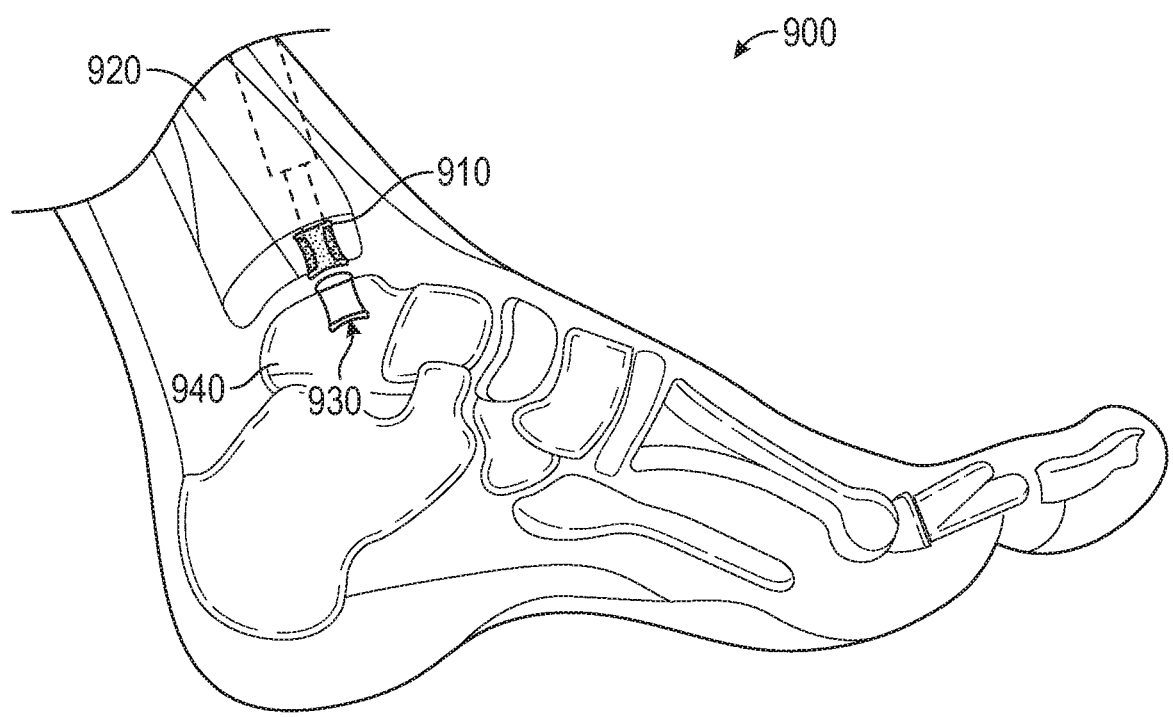

FIG. 9 illustrates another exemplary method for implanting bone implants.

Figure 10A:
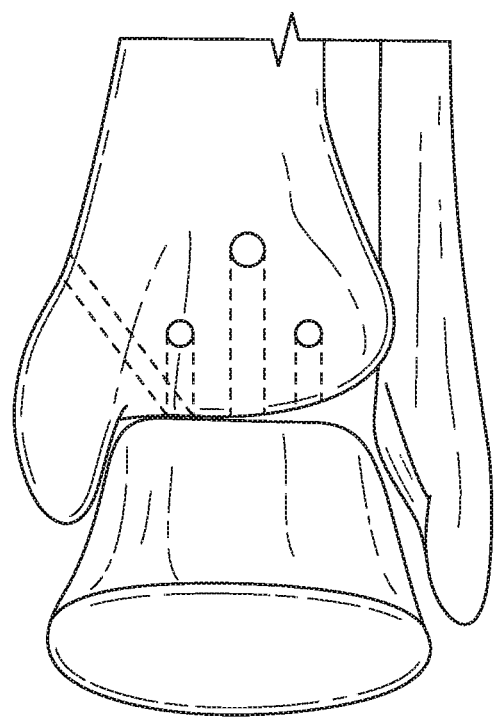
Figure 10B:
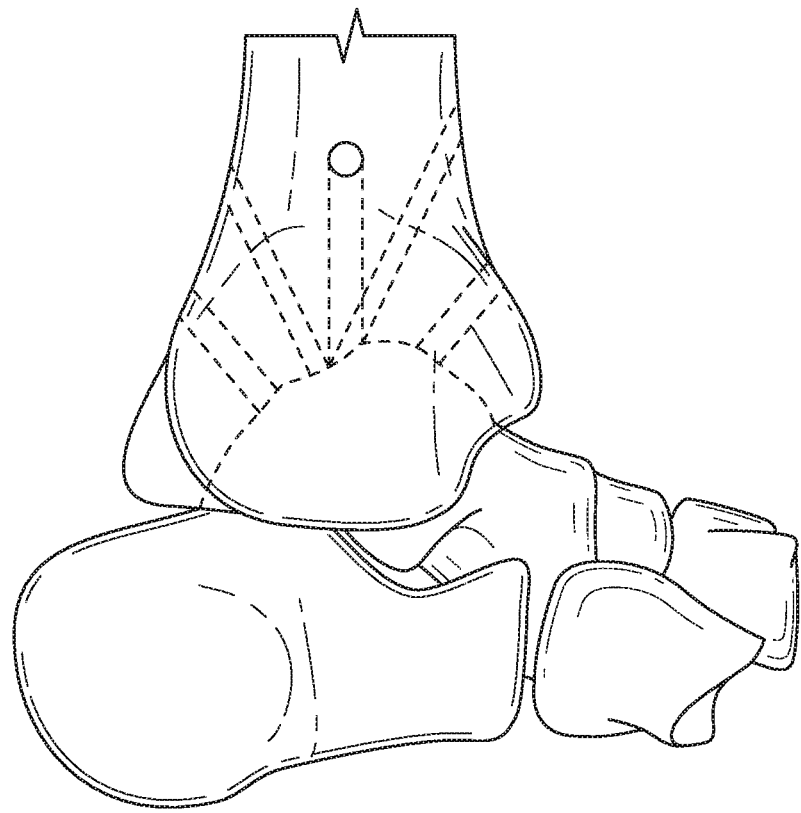

FIGS. 10A and 10B illustrate an anterior-posterior view and a medial-lateral view of various examples of access points.

Figure 11:
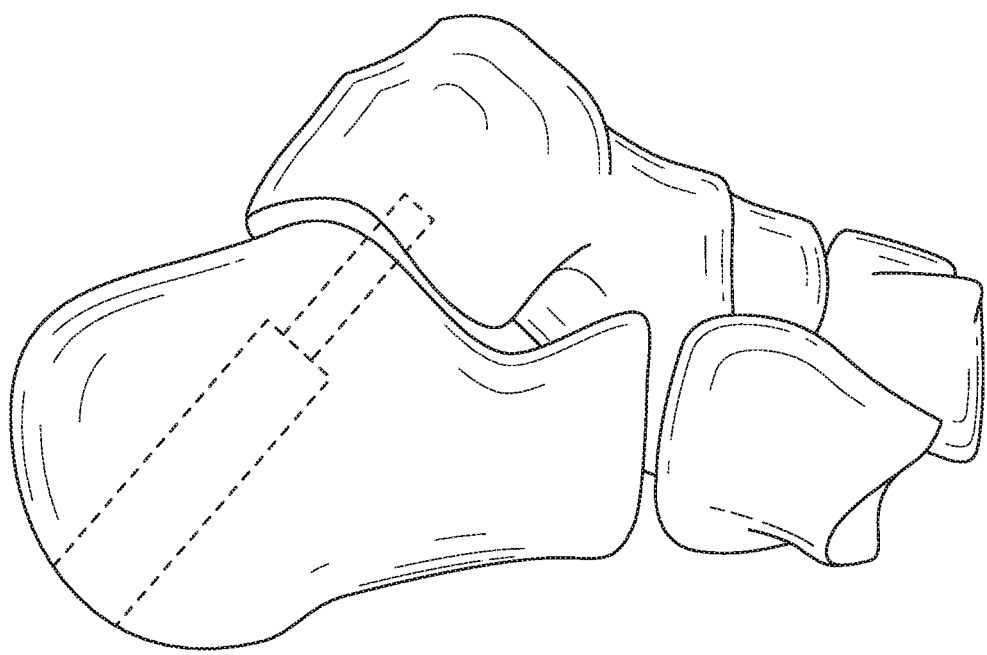

FIG. 11 illustrates another exemplary method for implanting bone implants.

Corresponding reference numerals indicate corresponding parts throughout the several views of the drawings.

DETAILED DESCRIPTION

Example embodiments will now be described more fully with reference to the accompanying drawings.

The present disclosure provides for an implant for insertion into and replacement of the damaged region of a talus bone and adjacent cartilage, the implant promoting bony in-growth while also providing for an articulable joint surface. Such implants can be used for surgical treatment of large, cystic lesions of the talus bone such as type-V lesions.

Figure 1A:
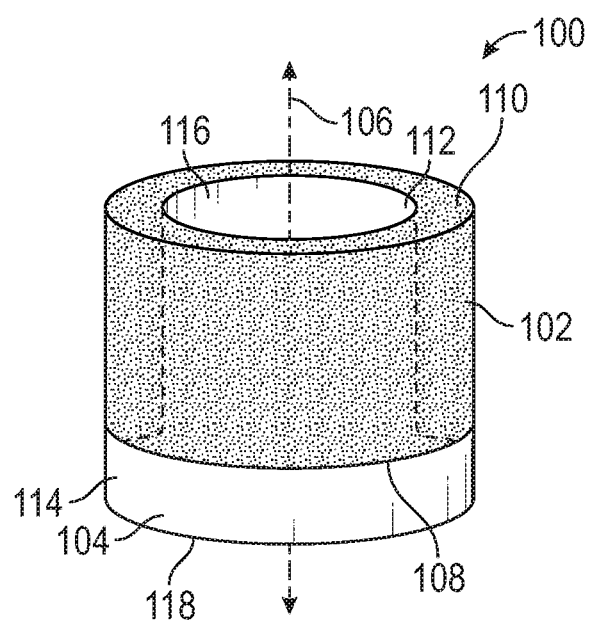
FIG. 1A illustrates a perspective view of an exemplary bone implant according to at least one example of the present description.
Figure 1B:
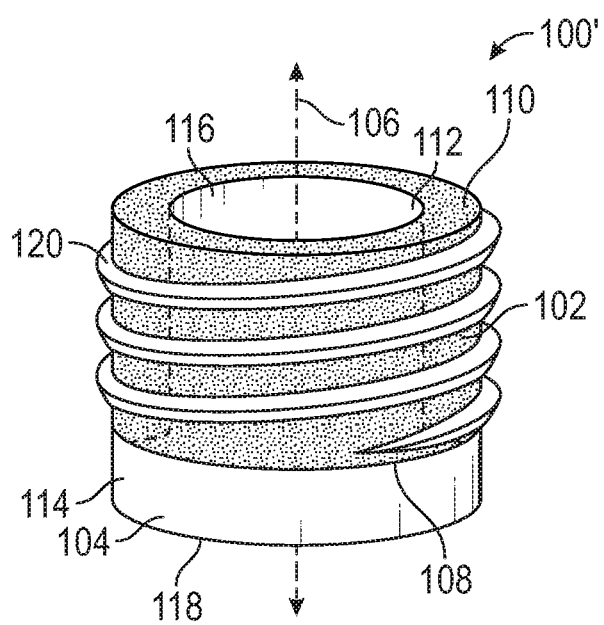
FIG. 1B illustrates a perspective view of another exemplary bone implant according to at least one example of the present description.

As illustrated in FIG. 1A-1B, the bone implant 100 (or 100' in all following instances) can be implanted in the talus in areas where osteochondral lesions are present. The bone implant 100 can comprise a cylindrical member 102 and an articulating member 104. The cylindrical member 102 can extend along an implant axis 106 from a first end 108 to an opposed second end 110. The cylindrical member 102 can have a void 112 disposed therein that extends from the first end 108 towards the second end 110. The articulating member 104 can comprise an articulating portion 114 and a core portion 116 extending away from the articulating portion. The articulating member 104 can be coupled to the cylindrical member 102 such that the core portion 116 extends into the void 112 disposed in the cylindrical member 102 and the articulating portion 114 is positioned adjacent the first end 108 of the cylindrical member 102. The articulating portion 114 can extend radially outward from the implant axis 106 to cover the first end 108 of the cylindrical member 102. The articulating member 104 can be monolithic. The articulating member 104 can comprise at least one of polyethylene, cobalt chrome, ceramic, hydrogel, polyurethane, silicone, or PEEK.

Figure 2A:
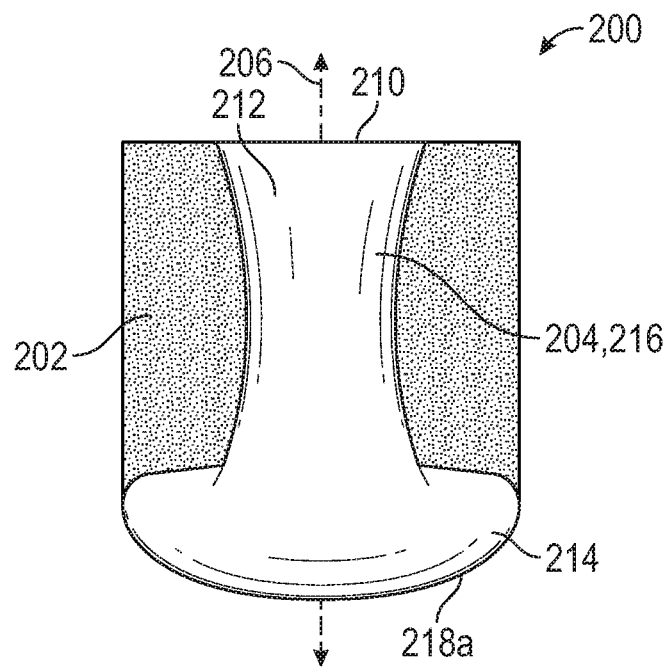
FIGS. 2A, 2B and 2C are cross-sectional side views of bone implants according to at least one example of the present description.
Figure 2B:
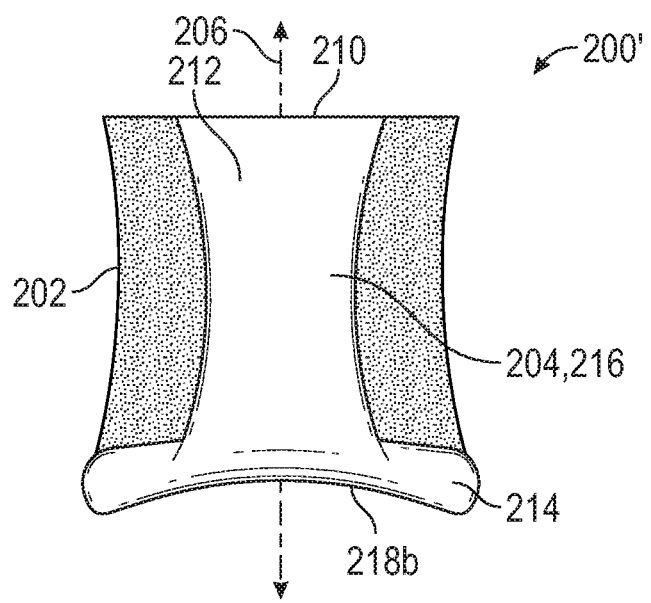

The articulating portion 114 can provide a surface to support articulation of a first bone (into which the implant 100 is implanted) and a second bone that is adjacent to the first bone. As illustrated in FIG. 1, the articulating portion 114 can have a generally planar articulating surface 118. As illustrated in FIG. 2A, the articulating portion 214 of implant 200 can have an articulating surface 218a that is at least partially concave relative to a plane transverse to the implant axis 106. Additionally or alternatively, as illustrated in FIG. 2B, the articulating portion 214 of implant 200' can have an articulating surface 218b that is at least partially convex relative to a plane transverse to the implant axis 206. Additionally, the void 212 disposed in the cylindrical member 202 and, additionally, the core portion 216 of the articulating member 204, can extend to the second end 210 of the cylindrical member 202.

Figure 2C:
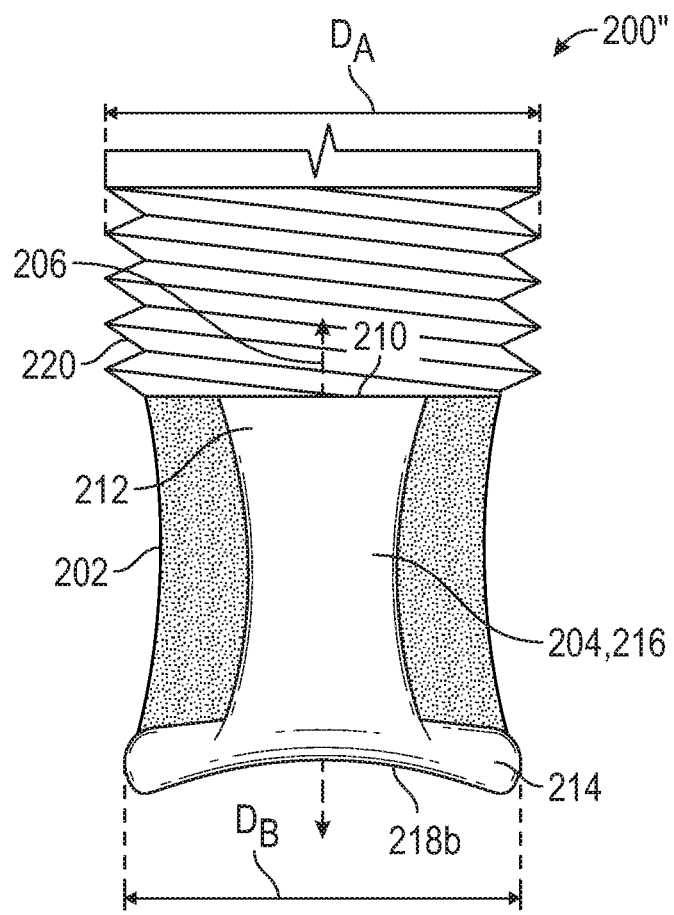

In an additional or alternative example illustrated in FIG. 1B, the implant 100' can have a helical thread 120 extending across at least a portion of the length of the cylindrical member 102. The helical thread 120 can be solid. The helical thread 120 can provide for benefits such as, for example and without limitation, initial stability, insertion options, and the like. In another additional or alternative example illustrated in FIG. 2C, the implant 200" can have a threaded member 220 coupled to the second end 210 of the cylindrical member 202. The threaded member 220 can be formed integrally with the cylindrical member 202, can be engageable with the cylindrical member 202, or can be a separate component from cylindrical member 202. The diameter of the threaded member $D_A$ can be greater than a diameter of the implant $D_B$. Either or both of the helical thread 120 and the threaded member 220 can be combined with any example of an implant disclosed herein.

The cylindrical member 102, 202 can comprise, in some examples, a material having interconnected open-pore structure for promoting bone tissue in-growth. The material can be at least one of stainless steel, titanium, titanium alloy, tantalum, polyether ether ketone (PEEK) and cobalt-chromium alloy. One suitable material comprises OsseoTi porous metal marketed by Zimmer Biomet (Warsaw, Ind.). OsseoTi comprises Ti6Al4V and can have a porous structure that generally mimics the porous structure of human cancellous bone. OsseoTi can be highly biocompatible and can have excellent corrosion resistance. Additionally or alternatively, the material can comprise Trabecular Metal, also marketed by Zimmer Biomet (Warsaw, Ind.). Such a material may be formed from a reticulated vitreous carbon foam substrate which can be infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are incorporated herein by reference. Such structures can be particularly suited for contacting bone and/or soft tissue, and in this regard, can be useful as bone substitutes and other implants and implant components that are receptive to cell and tissue ingrowth, for example, by allowing and promoting bony tissue or other tissue growth into the porous structure over time to enhance fixation (e.g., osseointegration) between the implant and surrounding bodily structures. According to various examples, the cylindrical member 102, 202 can comprise biologics such as demineralized bone matrix (DBM), bone morphogenetic proteins (BMP) and antibiotics. According to other features, the cylindrical member 102, 202 can comprise at least one of an anti-infective agent, an osteoconductive agent, an autologous blood product, a hydrogel, autologous cells, allogenic cells, peptides, and a bulk allograft.

Figure 3:
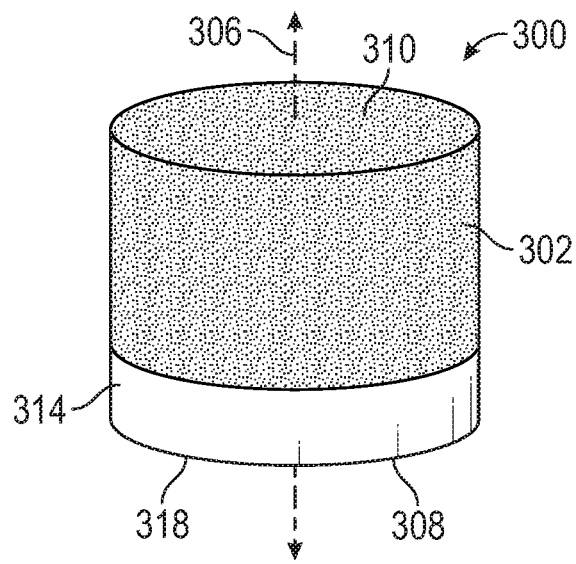
FIG. 3 illustrates a perspective view of a bone implant according to at least one example of the present description.

As illustrated in FIG. 3, the present disclosure also provides for a bone implant 300 that can comprise a cylindrical member 302 that can extend along an implant axis 306 from a first end 308 to an opposed second end 310 thereof. Cylindrical member 302 can comprise any material or combination of materials described above with reference to cylindrical member 102, 202. The region proximate the first end 308 of the cylindrical member 302 can comprise an articulating portion 314. The articulating portion 314 can be formed monolithically with the cylindrical member 302. The articulating portion 314 can comprise a non-porous variant of the material of the cylindrical member 302 such as, for example and without limitation, a titanium alloy, a tantalum alloy, and the like. Alternatively, the articulating portion 314 can be formed from a different material than the cylindrical member 302. For example, the articulating portion 314 can comprise cobalt chrome or other suitable metals. In some examples, the articulating portion 314 can comprise an articulating surface 318 that can comprise a polished metal or metal alloy. A polished articulating surface 318 can aid in articulation of the bone implant with less friction with adjacent surfaces (e.g., another implant or adjacent bone), and result in a longer lifetime of the implant.

As illustrated in FIG. 4, the present disclosure also provides for a system 400 comprising a first implant 410 for implantation into a first bone 420 of a joint and a second implant 430 for implantation into a second bone 440 of a joint. In one example, the system can be used with an ankle. Here, the first bone 420 can be a talus and the second bone 440 can be either a calcaneous or a tibia. In one example, an implant or a system comprising two implants can facilitate articulation of the talus with the calcaneous (in which case the talus implant will be positioned in the lower region of the talus). In another example, an implant or a system comprising two implants can facilitate articulation of the talus with the tibia (in which case the talus implant will be positioned in the upper region of the talus). The first implant 410 and the second implant 430 can each comprise any of the implants described above with reference to FIGS. 1-3. Further, the first implant 410 and the second implant 430 can be either the same as or different from each other.

In one example, the articulating surface 412 of the first implant 410 can be at least partially convex and the articulating surface 432 of the second implant 430 can be at least partially concave (or vice-versa) in order to aid in more effective articulation of the implants with respect to one another. In other examples, one or both of the articulating surfaces 412, 432 can be generally planar. Where the first and second bone implants 410, 430 at least partially directly oppose one another and articulate with respect to one another, one of the first or second articulating surfaces 412, 432 can comprise metal and the opposing first or second articulating surface can comprise polyethylene. Alternatively, each of the opposing first and second articulating surfaces 318, 338 can comprise metal, or each can comprise polyethylene.

Although FIG. 4 illustrates that articulating surface 412 of the first implant 410 directly opposes the articulating surface 432 of the second implant 430, this need not be the case. As illustrated in FIG. 5, the articulating surface 512 of the first implant 510 can be at least partially offset from the articulating surface 532 of the second implant 530, such that each implant at least partially articulates in direct contact with bone or surrounding tissue. Additionally or alternatively, the bones of the foot could be rotated relative to one another to achieve alignment of the implants 520, 530 to ensure an optimal therapeutic result.

In various other examples, three, four, five or potentially more implants can be used in an implantable system. As illustrated in FIG. 6, a system 600 can comprise, e.g., five bone implants: two implants 602, 604 in a first bone of the joint, and three implants 606, 608, 610 in an opposing bone of the joint. In this example, multiple implants can be prepared through a single access hole. As one example, implants 606 and 608 can be prepared through the access hole associated with implant 602, and implant 602 subsequently prepared. As another example, implants 608 and 610 can be prepared through the access hole associated with implant 604, and implant 604 subsequently prepared.

In another example, a drill guide 700 can be provided. The drill guide 700 can comprise a main body 702, a slotted sleeve 704 and a foot 708. The main body 702 can be angularly adjustable to rotate about axis 712 to change the angle between the foot 708 and the sleeve 704. The main body 702 can be angularly adjustable to rotate about axis 714 to change the angle between the foot 708 and the sleeve 704 in a second plane. The sleeve 704 can comprise two slotted telescoping sleeves to facilitate adjustability and removal from guide pin 706 after the guide pin 706 is placed into bone. The foot 708 can have an insertion end that is open and slotted. The foot 708 can facilitate identification of the defect in the native bone. The guide foot can have a dimensions a and b that can each be larger than the corresponding implant dimensions to, for example, ensure proper spacing between multiple guide pins and holes for implants.

In another example, at least FIGS. 8A, 8B, 9, and 11 illustrate one method for implanting bone implants. A drill having a first diameter D1 can make a first bore through a first bone of a joint and into the second bone of a joint opposite the first bone. A second drill having a second diameter D2 that is greater than the first diameter can make a counter bore into the first bone. The second implant can have a first diameter D1 corresponding to the first drill and can be inserted into a second bone of a joint. The first implant can have a second diameter D2 corresponding to the second drill and can be inserted into the first bone subsequent to insertion of the first implant. In one example shown in FIGS. 8A and 8B, the first implant 810 can be implanted in the first bone that can be a talus 820 and the second implant 830 can be implanted in the second bone that can be a tibia 840. In another example shown in FIG. 9, the first implant 910 can be implanted in first bone that can be a tibia 920 and a second implant 930 can be implanted in a second bone that can be a talus 940. In another example shown in FIG. 11, the first implant 910 can be implanted in first bone that can be a tibia 920 and a second implant 930 can be implanted in a second bone that can be a talus 940. As illustrated in FIGS. 10A and 10B, the number and examples of implant access strategies are numerous and one or more access points can be used to implant one or more implants. Hole placements in FIGS. 10A and 10B are exemplary only and are not intended to be limiting.

A method for implanting a bone implant, such as those configurations shown in at least FIGS. 4, 8A, 8B, 9, and 10, can comprise placing wires or drill holes from the first bone to the second bone. To ensure clarity of disclosure, in the following disclosure the tibia is the first bone and the talus is the second bone (unless specified otherwise), however any of the recited combination disclosed herein or known in the art can be employed using the methods described herein. The wires or drill holes can be placed over areas of articular defects to be treated. The articular defect can be on either the first bone or the second bone of the joint (e.g., the tibia or the talus). The guide wire can be inserted into the joint space through the tibia. A first hole can be drilled with a cannulated drill through the tibia to the joint space. The wire and drill can be removed. The location of the talus defect can be maintained in line with the tibia hole and a second solid drill can drill into the talus to set the depth of the second implant. The depth of the second implant can be, for example, from about 10 mm to about 20 mm. Optionally, a guide wire can be placed across the joint space and into the talus. Optionally, instead of the solid drill, the cannulated drill can drill through the tibia and into the talus to set the depth for an implant height for the second implant.

In an example where more than one implant is needed and as illustrated in FIG. 6, a second guide pin can be used to facilitate placement of a second pin. The same guide or a second guide can be used for the placement of the second pin. Additionally or alternatively, the same tibial hole can be used to facilitate placement for a plurality of talus implants. In one example illustrated in at least FIG. 5, the foot, with guide pins removed, can be rotated to align a location for the second talus hole with the tibial hole and the guide. Then, the guide pin can be placed and the second talus hole can be drilled at the aligned location.

In another example, a modular cutter or a reamer can be inserted into the joint space from a small incision. A cutter can be attached to a guide pin and can cut bone tissue to a desired depth in the talus and the tibia. A two-sided cutter can be used or a one-sided cutter can be used, requiring repositioning for each hole. Such methods are disclosed in U.S. Pat. No. 9,301,766, which is hereby incorporated by reference in its entirety.

In another example, a drill guide, such as the drill guide 700 illustrated in FIGS. 7A and 7B, comprising a drill over a pin 706 or wire can be employed. A first drill 704a can be used to drill a first hole through the talus and into the tibia. The second drill 704b can have a second diameter that is greater than the first diameter and can drill into the tibia only. This method allows additional fixation on the tibial implant using, for example, one of the implants of FIGS. 1B and 2C.

In another example, the joint between the calcaneous and the talus can be prepared and implanted similar to the talus/tibia examples above. If needed, a guide can be employed. The joint can be accessed and lesions identified. A guide wire can be placed. An implant hole or holes can be drilled. Here, the calcaneous can be over drilled through the first cortex if an implant with adjustment or additional fixation is to be employed using, for example, one of the implants of FIGS. 1B and 2C.

Various Notes & Examples

Example 1 is a bone implant, comprising: a cylindrical member that can extend along an implant axis from a first end to an opposed second end thereof. The cylindrical member can have a void disposed therein that can extend from the first end towards the second end. The cylindrical member can comprise an interconnected open-pore structure for promoting bone tissue in-growth. An articulating member can comprise an articulating portion and a core portion extending away from the articulating portion. The articulating member can be coupled to the cylindrical member such that the core portion extends into the void disposed in the cylindrical member. The articulating portion can be positioned adjacent the first surface of the cylindrical member and can extend radially outward from the implant axis to cover the first surface of the cylindrical member.

In Example 2, the subject matter of Example 1 optionally includes wherein the articulating member can be monolithic.

In Example 3, the subject matter of any one or more of Examples 1-2 optionally include wherein the articulating member comprises at least one of polyethylene and cobalt chrome.

In Example 4, the subject matter of any one or more of Examples 1-3 optionally include wherein an articulating surface of the articulating portion can be at least partially concave relative to a plane transverse to the implant axis.

In Example 5, the subject matter of any one or more of Examples 1-4 optionally include wherein an articulating surface of the articulating portion can be at least partially convex relative to a plane transverse to the implant axis.

In Example 6, the subject matter of any one or more of Examples 1-5 optionally include wherein the cylindrical member comprises at least one of a titanium alloy and a tantalum alloy.

In Example 7, the subject matter of any one or more of Examples 1-6 optionally include wherein the void disposed in the cylindrical member extends to the opposed second surface, and wherein the elongate core of the articulating member extends to the opposed second surface of the cylindrical member.

Example 8 is a system comprising a first bone implant and a second bone implant. The first bone implant can comprise a first cylindrical member having an outer diameter and can extend along an implant axis from a first end to an opposed second end thereof. The first cylindrical member can have a void disposed therein extending from the first end towards the second end. The first cylindrical member can comprise an interconnected open-pore structure for promoting bone tissue in-growth. The first bone implant can further comprise a first articulating member that can comprise an articulating portion and a core portion extending away from the articulating portion. The first articulating member can be coupled to the first cylindrical member such that the core portion extends into the void disposed in the first cylindrical member. The articulating portion can be positioned adjacent the first surface of the first cylindrical member and can extend radially outward from the implant axis to cover the first surface of the first cylindrical member. A second bone implant can comprise a second cylindrical member that can have an outer diameter and can extend along an implant axis from a first end to an opposed second end thereof. The second cylindrical member can comprise an interconnected open-pore structure for promoting bone tissue in-growth. The second bone implant can further comprise an articulating portion proximate the first end of the second cylindrical member. The outer diameter of the first cylindrical member of the first bone implant can be less than the outer diameter of the second cylindrical member of the second bone implant.

In Example 9, the subject matter of Example 8 optionally includes wherein either or both of the first cylindrical member and the second cylindrical member can comprise at least one of titanium, a titanium alloy, tantalum, and a tantalum alloy.

In Example 10, the subject matter of any one or more of Examples 8-9 optionally include wherein the articulating portion and the second cylindrical member of the second bone implant can be monolithic.

In Example 11, the subject matter of any one or more of Examples 8-10 optionally include wherein the articulating portion of the second bone implant can comprise a non-porous metal or a metal alloy.

In Example 12, the subject matter of any one or more of Examples 8-11 optionally include wherein the second cylindrical member further comprises a void disposed therein that can extend from the first end towards the second end; and wherein the second implant further comprises a second articulating member comprising the articulating portion and a core portion that can extend away from the articulating portion, wherein the second articulating member can be coupled to the second cylindrical member such that the core portion can extend into the void disposed in the second cylindrical member and the articulating portion can be positioned adjacent the first surface of the second cylindrical member and can extend radially outward from the implant axis to cover the first surface of the second cylindrical member.

In Example 13, the subject matter of any one or more of Examples 8-12 optionally include wherein an articulating surface of the articulating portion of the first articulating member can be at least partially concave relative to a plane transverse to the implant axis.

In Example 14, the subject matter of Example 13 optionally includes wherein an articulating surface of the articulating portion of the second articulating member can be at least partially convex relative to a plane transverse to the implant axis.

In Example 15, the subject matter of any one or more of Examples 8-14 optionally include wherein an articulating surface of the articulating portion of the first articulating member can be at least partially convex relative to a plane transverse to the implant axis.

In Example 16, the subject matter of Example 15 optionally includes wherein an articulating surface of the articulating portion of the second articulating member can be at least partially concave relative to a plane transverse to the implant axis.

In Example 17, the subject matter of any one or more of Examples 8-16 optionally include wherein at least one of the first the articulating member and the second articulating member can be monolithic.

In Example 18, the subject matter of any one or more of Examples 8-17 optionally include wherein at least one of the first the articulating member and the second articulating member can comprise at least one of polyethylene and cobalt chrome.

In Example 19, the subject matter of any one or more of Examples 8-18 optionally include wherein the cylindrical member can comprise at least one of a titanium alloy and a tantalum alloy.

In Example 20, the subject matter of any one or more of Examples 8-19 optionally include wherein the void disposed in the first cylindrical member can extend to the opposed second surface, and wherein the elongate core of the first articulating member can extend to the opposed second surface of the first cylindrical member.

In Example 21, the subject matter of any one or more of Examples 8-20 optionally include wherein the void disposed in the second cylindrical member can extend to the opposed second surface, and wherein the elongate core of the second articulating member can extend to the opposed second surface of the second cylindrical member.

Each of these non-limiting examples can stand on its own, or can be combined in various permutations or combinations with one or more of the other examples. In the examples, the terms "a" and "the" are used interchangeably, such that reference to "the bone implant" in a given example can refer to a bone implant described in a previous example that is optionally combined with the given example, or can refer to a separate bone implant entirely. Similarly "a bone implant" can refer to a newly introduced bone implant, or to a bone implant described in a previous example.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be comprised within the scope of the disclosure.

What is claimed is:

1. An ankle bone implant, comprising:
    a cylindrical member extending along an implant axis from a first end to an opposed second end thereof,
        the cylindrical member having a void disposed therein extending from the first end to the second end,
        the void having a cross-sectional diameter taken orthogonal to the implant axis,
        the cross-sectional diameter continuously and smoothly varying in value at locations along the implant axis from the first end to the second end,
        the cross-sectional diameter becoming maximum only at at least one of the first end and the second end,
        the cylindrical member comprising an interconnected open-pore structure for promoting bone tissue in-growth; and
    an articulating member comprising an articulating portion and a core portion extending away from the articulating portion, the articulating member being coupled to the cylindrical member such that:
        the core portion extends into the void disposed in the cylindrical member,
        the core portion has a cross-sectional diameter that, varies in value at locations along the implant axis from the first end to the second end and substantially matches the cross-sectional diameter of the void at each location along the implant axis from the first end to the second end, and
        the articulating portion is positioned adjacent a first surface of the cylindrical member and extends radially outward from the implant axis to cover the first surface of the cylindrical member.

2. The ankle bone implant of claim 1, wherein the articulating member is monolithic.

3. The ankle bone implant of claim 1, wherein the articulating member comprises at least one of polyethylene and cobalt chrome.

4. The ankle bone implant of claim 1, wherein an articulating surface of the articulating portion is at least partially concave relative to a plane transverse to the implant axis.

5. The ankle bone implant of claim 4, wherein the at least partially concave articulating surface is shaped to contact an at least partially convex articulating surface of the corresponding ankle bone implant implanted into the tibia of the ankle joint.

6. The ankle bone implant of claim 1, wherein an articulating surface of the articulating portion is at least partially convex relative to a plane transverse to the implant axis.

7. The ankle bone implant of claim 1, wherein the cylindrical member comprises at least one of a titanium alloy and a tantalum alloy.

8. The ankle bone implant of claim 1, wherein the elongate core of the articulating member extends to the opposed second end of the cylindrical member.

9. An ankle bone implant, comprising:
a cylindrical member extending along an implant axis from a first end to an opposed second end thereof,
the cylindrical member having a void disposed therein extending from the first end towards the second end,
the void having a cross-sectional diameter taken orthogonal to the implant axis,
the cross-sectional diameter continuously and smoothly decreasing from the first end to a waist positioned between the first and second ends,
the cross-sectional diameter continuously and smoothly increasing from the waist to the second end,
the cylindrical member comprising an interconnected open-pore structure for promoting bone tissue ingrowth; and
an articulating member comprising an articulating portion and a core portion extending away from the articulating portion, the articulating member being coupled to the cylindrical member such that:
the core portion extends into the void disposed in the cylindrical member,
the core portion has a varying cross-sectional diameter along the implant axis such that a contour of the core portion mirrors a contour of the void from the first end to the second end, and
the articulating portion is positioned adjacent a first surface of the cylindrical member and extends radially outward from the implant axis to cover the first surface of the cylindrical member.

10. The ankle bone implant of claim 9, wherein the articulating member is monolithic.

11. The ankle bone implant of claim 9, wherein the articulating member comprises at least one of polyethylene and cobalt chrome.

12. The ankle bone implant of claim 9, wherein an articulating surface of the articulating portion is at least partially concave relative to a plane transverse to the implant axis.

13. The ankle bone implant of claim 12, wherein the at least partially concave articulating surface is shaped to contact an at least partially convex articulating surface of the corresponding ankle bone implant implanted into the calcaneous of the ankle joint.

14. The ankle bone implant of claim 9, wherein the cylindrical member comprises at least one of a titanium alloy and a tantalum alloy.

15. The ankle bone implant of claim 9, wherein the void disposed in the cylindrical member extends to the opposed second end, and wherein the elongate core of the articulating member extends to the opposed second end of the cylindrical member.

16. An ankle bone implant, comprising:
a cylindrical member extending along an implant axis from a first end to an opposed second end thereof,
the cylindrical member having a void disposed therein extending from the first end to the second end,
the void having a cross-sectional diameter taken orthogonal to the implant axis,
the cross-sectional diameter continuously and smoothly varying in value at locations along the implant axis from the first end to the second end,
the cross-sectional diameter becoming maximum only at at least one of the first end and the second end,
the cylindrical member comprising an interconnected open-pore structure for promoting bone tissue ingrowth; and
an articulating member comprising an articulating portion and a core portion extending away from the articulating portion,
the articulating portion having an articulating surface that is at least partially concave,
the articulating member being coupled to the cylindrical member such that:
the core portion extends into the void disposed in the cylindrical member,
the core portion has a varying cross-sectional diameter along the implant axis such that a contour of the core portion mirrors a contour of the void from the first end to the second end, and
the articulating portion is positioned adjacent a first surface of the cylindrical member and extends radially outward from the implant axis to cover the first surface of the cylindrical member.

17. The ankle bone implant of claim 16, wherein the articulating surface is at least partially concave relative to a plane that is orthogonal to the implant axis.

18. The ankle bone implant of claim 16, wherein:
the cylindrical member has an outer diameter taken orthogonal to the implant axis; and
the outer diameter is substantially constant at the locations along the implant axis from the first end to the second end.

* * * * *

UNITED STATES PATENT AND TRADEMARK OFFICE
CERTIFICATE OF CORRECTION

PATENT NO. : 11,103,358 B2　　　　　　　　　　　　　　　　　　　　　　Page 1 of 1
APPLICATION NO. : 15/349752
DATED : August 31, 2021
INVENTOR(S) : Anderson et al.

It is certified that error appears in the above-identified patent and that said Letters Patent is hereby corrected as shown below:

In the Claims

In Column 10, Line 26, in Claim 1, delete "at at" and insert --at-- therefor

In Column 10, Line 36, in Claim 1, delete "that," and insert --that-- therefor

In Column 12, Line 16, in Claim 16, delete "at at" and insert --at-- therefor

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*